United States Patent
Hwang et al.

(10) Patent No.: US 11,896,601 B2
(45) Date of Patent: Feb. 13, 2024

(54) COMPOSITION FOR PREVENTION OR TREATMENT OF ALLERGIC DISEASE INCLUDING INOTODIOL COMPOUND AS ACTIVE INGREDIENT

(71) Applicant: CARBOEXPERT INC., Daejeon (KR)

(72) Inventors: In Kyu Hwang, Yongin-si (KR); Young Ho Kim, Daejeon (KR); Thi Minh Nguyet Nguyen, Daejeon (KR); Jong Seong Kang, Daejeon (KR)

(73) Assignee: CARBOEXPERT INC., Daejeon (KR)

( * ) Notice: Subject to any disclaimer, the term of this patent is extended or adjusted under 35 U.S.C. 154(b) by 706 days.

(21) Appl. No.: 17/050,878

(22) PCT Filed: May 24, 2018

(86) PCT No.: PCT/KR2018/005906
§ 371 (c)(1),
(2) Date: Oct. 27, 2020

(87) PCT Pub. No.: WO2019/225783
PCT Pub. Date: Nov. 28, 2019

(65) Prior Publication Data
US 2021/0369736 A1    Dec. 2, 2021

(51) Int. Cl.
*A61K 31/575* (2006.01)
*A23L 33/105* (2016.01)
*A61P 37/08* (2006.01)
*A61K 36/07* (2006.01)

(52) U.S. Cl.
CPC .......... *A61K 31/575* (2013.01); *A23L 33/105* (2016.08); *A61K 36/07* (2013.01); *A61P 37/08* (2018.01)

(58) Field of Classification Search
CPC .................................................... A61K 31/575
USPC ............................................................ 514/182
See application file for complete search history.

(56) References Cited

FOREIGN PATENT DOCUMENTS

| JP | 2006-347991 A | 12/2006 |
|---|---|---|
| KR | 10-2006-0023227 A | 3/2006 |
| KR | 10-2013-0037154 A | 4/2013 |
| KR | 10-1351054 B1 | 1/2014 |
| KR | 10-2018-0003002 A | 1/2018 |

OTHER PUBLICATIONS

Yoon, Take Joon et al., "Inhibitory effect of chaga mushroom extract on compound 48/80-induced anaphylactic shock and IgE production in mice", *International Immunopharmacology*, vol. 15, Issue 4, Apr. 2013 (pp. 666-670).

Minh Nguyen Nguyet, Thi et al., "The mast cell stabilizing activity of Chaga mushroom critical for its therapeutic effect on food allergy is derived from inotodiol", *International Immunopharmacology*, vol. 54, Jan. 2018, (pp. 286-295).

International Search Report dated May 9, 2019 in counterpart International Patent Application No. PCT/KR2018/005906 (3 pages in English and 3 pages in Korean).

*Primary Examiner* — Raymond J Henley, III
(74) *Attorney, Agent, or Firm* — NSIP Law

(57) ABSTRACT

Provided is a composition for prevention or treatment of an allergic disease, the composition including an inotodiol compound and a chaga mushroom (*Inonotus obliquus*) extract including an inotodiol compound as an active ingredient. More particularly, it was found that when an inotodiol compound or a chaga mushroom extract containing an inotodiol compound as one of the active ingredients is administered to a mouse model in which a food allergy was induced, symptoms induced by the allergy were alleviated and cured. Thus, the inotodiol compound or the chaga mushroom extract containing an inotodiol compound as an active ingredient is expected to be useful as a composition for prevention or treatment of an allergic disease.

11 Claims, 8 Drawing Sheets

COMPOSITION FOR PREVENTION OR TREATMENT OF ALLERGIC DISEASE INCLUDING INOTODIOL COMPOUND AS ACTIVE INGREDIENT

CROSS REFERENCE TO RELATED APPLICATIONS

This application is a U.S. National Stage Application of International Application No. PCT/KR2018/005906, filed on May 24, 2018, the entire disclosure of which is incorporated herein by reference for all purposes.

TECHNICAL FIELD

The present disclosure relates to a composition for prevention or treatment of an allergic disease, the composition including a chaga mushroom extract containing an inotodiol compound as an active ingredient or an inotodiol compound.

BACKGROUND ART

An allergy is a hypersensitivity reaction, which refers to a phenomenon that occurs rapidly in vivo due to an antigen-antibody reaction when an organism comes into contact with a foreign material. An antigen that induces an allergic response is referred to as an allergen. Typical allergens are pollen, medicines, vegetable fibers, bacteria, food, dyes, and chemicals.

With the development of modern civilization, the chance of exposure to various allergens has increased, and the number of patients complaining of allergy symptoms is increasing rapidly. It is known that the number of patients with allergies is higher in advanced countries, and in Korea, although there is no accurate statistical data, the number of patients is increasing every year. In particular, the number of pediatric patients is known to be increasing rapidly. For this reason, many domestic and foreign pharmaceutical companies and research institutes have invested a lot of resources in the development of causative drugs that can reduce the economic, physiological, and psychological burden caused by allergic diseases. However, the development of fundamental treatments has not yet been achieved.

Until now, immune hypersensitivity has been classified into four major types. Type I hypersensitivity is allergic hypersensitivity mediated by specific IgE antibodies. Specific IgE antibodies bind to mast cells or surface receptors of basophils, followed by secretion of mediators from the cells, which causes immediate hypersensitivity reactions such as asthma, allergic rhinitis, and anaphylaxis. Type II hypersensitivity is a response mediated by specific IgG antibodies, and the reaction is initiated by antibodies that react with an antigenic component on a cell surface. Type III hypersensitivity is a cytotoxic reaction that occurs when there is a lot of antigen, wherein antigens and antibodies form complexes and activate complement. Type IV hypersensitivity is T cell-mediated hypersensitivity mediated by T cells.

Mast cells are the main cells that cause allergic reactions. Mast cells are activated when immunoglobulin E (IgE) combines with an allergen. Mast cells secrete various mediators and cause mucosal edema, bronchial smooth muscle contraction, and mucus secretion, thereby contributing to the reaction. Such mast cells have been found to play an important role in maintaining and defending the immune system in the human body, and are located in tissues surrounding respiratory organs, digestive organs, genitourinary organs, dermis, and blood vessels (Rivera, J., et al., 2008; Moon, T. C., et al., 2010; Blank, U., et al., 2013; Boyce, J. A., 2004).

Due to external stimulation, mast cells produce and secrete mediators that cause allergic inflammatory responses. Such mediators include mediators preformed in granules produced prior to stimulation, and newly synthesized mediators produced following stimulation (Schwartz, L. B., et al., 1998).

Histamine, proteoglycans, serine-proteases, carboxypeptidase A, sulfatases, and exoglycosidases are preformed and present in granules of mast cells. Upon stimulation, these materials are secreted to the outside of the cells. One of the most important materials that are newly produced and synthesized after mast cells are stimulated is a metabolite derived from arachidonic acid, e.g., prostaglandin $D_2$ ($PGD_2$) and leukotriene $C_4$ ($LTC_4$), $LTD_4$, and $LTE_4$. In addition, platelet-activating factor (PAF) is also important (Kangmo Ahn, 2004).

It was found that mast cells are not only limited to early allergic responses but also deeply related to late allergic responses and chronic allergic responses. In other words, tumor necrosis factor-α (TNF-α) produced and secreted from mast cells increases the expression of adhesion molecules of vascular endothelial cells and promotes the inflow of eosinophils and T lymphocytes into a target organ. In addition, interleukin (IL)-4, IL-13, and IL-6 produced by mast cells increase the response of T helper type 2 (Th2) cells and eventually increase production of IgE, thereby contributing to chronic allergic responses. As such, mast cells play a central role in causing and sustaining an allergic inflammatory response (Kangmo Ahn, 2004).

Traditionally, three treatment methods such as allergen avoidance, drug therapy, and allergen immunotherapy are known as the main methods of treating allergic diseases. In fact, the most commonly used pharmacologic therapy for allergic diseases is the use of inhibitors (antihistamine agent, anti-leukotriene agent, etc.) for chemical mediators (histamine, leukotriene, etc.) that are involved in allergic responses or the use of anti-inflammatory drugs (steroids, immunosuppressants, etc.) that suppress inflammation of tissues caused by allergic responses. However, these pharmacologic therapies have a disadvantage in that it is only possible to maintain improved clinical symptoms when the drug is administered continuously (Nahm, D. H., 2015). It is well known that long-term use of steroids causes various side effects. Thus, much attention is needed when using steroids.

Recently, as therapeutic agents for allergic diseases, there is a growing interest in mast cell stabilizers that inhibit degranulation of mast cells. A mast cell stabilizer inhibits mast cell degranulation and has an advantage in that it obtains the effects of an antihistamine agent and an anti-leukotriene agent at the same time, but has been developed insufficiently as compared with other drugs. Chromogenic materials such as cromoglycate and nedocromil have been developed as mast cell stabilizers, but the uses thereof are limited due to the inconvenience of use due to low bioavailability when administered orally and the ambiguity of the mechanism (Finn, D. F., et al., 2013). Therefore, there is a need to develop a mast cell stabilizer which is mast cell-selective, safe, and effective.

Chaga mushroom (*Inonotus obliquus*) belongs to Hymenochaetaceae (Basidiomycota, Aphyllophorales), which grows wild in stalks and stumps of birch, alder, and rowan in the northern hemisphere where the weather is cold and humid, such as in Siberia in Russia, Finland, Norway, Ukraine, Hokkaido in Japan, and Mount Odae in Korea. Chaga mushroom is a white rot fungus that decomposes lignin, cellulose, and hemicellulose. Chaga mushroom is known to be parasitic and forms black sclerotia in stalks of a host such as birch. (Guk M H., et al., 2013).

From the late 1950's, when research began in Russia, it has been reported that materials such as β-glucan, polyphenol, and sterol extracted from fruiting bodies of chaga mushroom have shown physiological activity in human bodies. In addition to anti-cancer effects (Youn M J., et al., 2008; Nomura M., et al., 2008), chaga mushroom was found to exhibit antioxidant activity (Park Y K, et al., 2004), anti-hyperlipidemia activity, anti-diabetic activity (Kim M A, et al., 2009), antifungal activity, antiviral activity, anti-inflammatory activity, and analgesic effects.

Studies have been carried out to isolate useful compounds from chaga mushrooms with various physiological activities. Various compounds such as inotodiol, trametenolic acid, lanosterol, and inonotsulide were found to be isolated (Ma L., et al., 2013). Among these compounds, the inotodiol compound was found to exhibit anti-cancer, anti-inflammatory, and melanogenesis suppression activities.

Accordingly, the present inventors found that an inotodiol compound isolated from a chaga mushroom extract or a chaga mushroom extract containing an inotodiol compound as an active ingredient improves and treats symptoms caused by an allergy in a food allergy-induced mouse model and inhibits mast cell immunoreactivity, thereby completing the present disclosure.

As prior art, Japanese Laid-Open Patent Publication 2006-347991 discloses that mushroom mycelia-derived materials including chaga mushroom inhibit release of histamine, which is a material related to allergy induction. The feature thereof is similar to that of the present disclose; however, the inotodiol compound is not described therein. In addition, Korean Patent Registration No. 11351054 discloses that an herbal composition containing chaga mushroom has an effect of treating atopic dermatitis, and chaga mushroom enhances overall immunity to fundamentally treat atopic dermatitis. However, the inotodiol compound is not described therein. Korean Patent Publication No. 2018-0003002 discloses that an inotodiol compound isolated from a chaga mushroom extract has an anti-inflammatory or therapeutic effect. However, allergy prevention or treatment and inhibitory effects on mast cell immunoreactivity are neither described nor implied therein.

DESCRIPTION OF EMBODIMENTS

Technical Problem

Provided is a composition for prevention or treatment of an allergic disease, wherein the composition is effective, safe, and subject to oral administration and includes a chaga mushroom extract containing an inotodiol compound as an active ingredient or an inotodiol compound.

Solution to Problem

According to an aspect of the present disclosure, a pharmaceutical composition for prevention or treatment of an allergic disease may include a chaga mushroom (*Inonotus obliquus*) extract including an inotodiol compound represented by Formula 1 as an active ingredient.

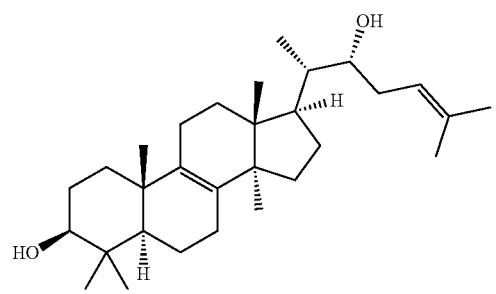

Formula 1

The chaga mushroom extract may be at least one selected from the group consisting of dichloromethane fractions or chloroform fractions obtained by adding dichloromethane or chloroform to an extract obtained by extracting chaga mushroom with 70 percent (%) ethanol as a solvent, respectively.

According to an aspect of the present disclosure, a pharmaceutical composition for prevention or treatment of an allergic disease may include an inotodiol compound represented by Formula 1 as an active ingredient.

The pharmaceutical composition may suppress degranulation of mast cells.

The allergic disease may be induced by at least one selected from the group consisting of pollen, medicines, vegetable fibers, bacteria, food, dyes, and chemicals. Preferably, the allergic disease may be induced by food.

The allergic disease may be at least one selected from the group consisting of urticaria, anaphylaxis, allergic rhinitis, bronchial asthma, and atopic dermatitis.

According to an aspect of the present disclosure, a health functional food composition for prevention or improvement of an allergic disease may include a chaga mushroom (*Inonotus obliquus*) extract including an inotodiol compound represented by Formula 1 as an active ingredient.

According to an aspect of the present disclosure, a health functional food composition for prevention or improvement of an allergic disease may include an inotodiol compound represented by Formula 1 as an active ingredient.

The present disclosure Will be described in further detail.

The present disclosure relates to a composition for prevention or treatment of an allergic disease, wherein the composition may include a chaga mushroom (*Inonotus obliquus*) extract including an inotodiol compound represented by Formula 1 as an active ingredient.

The chaga mushroom extract may be a fraction obtained by adding an organic solvent to an extract obtained by extracting chaga mushroom with 70 percent (%) ethanol as a solvent.

The organic solvent may be at least one selected from the group consisting of a C1 to C4 lower alcohol, dichloromethane, chloroform, ethyl acetate, diethyl acetate, diethyl ether, acetone, and hexane. However, the organic solvent is not limited thereto. The C1 to C4 lower alcohols may be methanol, ethanol, propanol, isopropanol, or butanol.

Preferably, the chaga mushroom extract may be at least one selected from the group consisting of dichloromethane fractions or chloroform fractions obtained by adding dichloromethane or chloroform to an extract obtained by extracting chaga mushroom is extracted with 70 percent (%) ethanol as a solvent, respectively.

The present disclosure relates to a composition for prevention or treatment of an allergic disease, wherein the composition may include an inotodiol compound represented by Formula 1 as an active ingredient.

The inotodiol compound may be synthesized according to a commonly known method and prepared as a pharmaceutically acceptable salt, or isolated or purified from a chaga mushroom extract.

The inotodiol compound isolated from the chaga mushroom may be purified through chromatography. The chromatography may be selected from silica gel column chromatography, HP-20 column chromatography, RP-18 column chromatography, LH-20 column chromatography, and high-performance liquid chromatography.

The allergy is a phenomenon that abruptly occur in vivo caused by an antigen-antibody reaction upon a contact with an allergen that is an allergy-inducing material. The allergen may be at least one selected from the group consisting of pollen, medicines, vegetable fibers, bacteria, food, dyes, and chemicals, and preferably, food. However, the allergen is not limited thereto.

Also, the allergic disease is caused by allergy, and examples thereof include bronchial asthma, allergic rhinitis, atopic dermatitis, urticaria, food allergy, drug allergy, serum sickness, and the like. The allergic disease has various types depending on a type of allergen and a type of a tissue that cause an allergic response.

The allergic disease may be at least one selected from the group consisting of urticaria, anaphylaxis, allergic rhinitis, bronchial asthma, and atopic dermatitis. However, the allergic disease is not limited thereto.

The inotodiol compound or the chaga mushroom extract containing an active ingredient may suppress degranulation of mast cells.

When the mast cell receives a stimulation from by an allergen, an allergy inflammatory response-inducing material such as histamine, serine-proteases, proteoglycans, prostaglandins $D_2$, and leukotrienes may be secreted to outside a cell, and this reaction is referred to as degranulation of mast cells. Therefore, inhibition of degranulation of mast cells by the inotodiol compound or the chaga mushroom extract containing an inotodiol compound as an active ingredient may inhibit secretion of an allergy inflammatory response-inducing material due to allergen stimulation, thereby preventing or treating allergy. This is referred to as a 'mast cell stabilizer'.

Particularly, the inotodiol compound of the present disclosure does not influence to activity regulation of $CD4^+T$ cell, and $CD8^+$cell, B cell, and macrophage but selectively inhibits degranulation of mast cells only, among $CD4^+T$ cell, CD8+ cell, B cell, macrophage, and a mast cell, which are related to allergy treatment.

The present disclosure relates to a pharmaceutical composition for prevention or treatment of an allergic disease, wherein the pharmaceutical composition may include an inotodiol compound or a chaga mushroom extract including an inotodiol compound as an active ingredient.

The pharmaceutical composition may include an inotodiol compound or a chaga mushroom extract including an inotodiol compound as an active ingredient in a range of 0.001 percent by weight (wt %) to 100 wt %.

The pharmaceutical composition may be formulated in the form of oral preparations such as powders, granules, tablets, capsules, suspensions, emulsions, syrups, and aerosols, external preparations, suppositories, or sterilized injection solutions, according to a conventional method. The pharmaceutical composition may include a carrier, an excipient, and a diluent, e.g., lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinyl pyrrolidone, water, methyl hydroxybenzoate, propyl hydroxybenzoate, talc, magnesium stearate, or mineral oil. In the case of formulation, a diluent or an excipient, e.g., a filler, an extender, a binder, a wetting agent, a disintegrant, and a surfactant, which are typically used, may be used. A solid preparation for oral administration may include a tablet, a pill, powder, granules, and a capsule. Such solid preparation may be prepared by mixing the inotodiol compound or the chaga mushroom extract including an inotodiol compound as an active ingredient with at least one selected from an excipient, e.g., starch, calcium carbonate, sucrose, lactose, or gelatin. In addition to simple excipients, lubricants, such as magnesium stearate talc. A liquid preparation for oral administration may include a suspension, an oral solution, an emulsion, and syrup and further include various excipients, e.g., a humectant, a sweetener, a flavoring agent, and a preservative, in addition to simple diluents, e.g., water and liquid paraffin, which are generally used. A preparation for parenteral administration may include sterilized aqueous solutions, non-aqueous solutions, suspensions, emulsions, freeze-dried preparations, or suppositories. Examples of the non-aqueous solution and suspension include propylene glycol, polyethylene glycol, vegetable oil such as olive oil, injectable ester such as ethyl oleate, and the like. A base of the suppository may be witepsol, macrogol, tween 61, cacao butter, laurin butter, or glycerogelatin.

The dosage of the pharmaceutical composition of the present disclosure may vary depending on the age, sex, body weight of the subject to be treated, the particular disease or pathological condition to be treated, the severity of the disease or pathological condition, the route of administration, and the judgment of the prescriber. Dosage may be determined based on these factors within the level of one of ordinary skill in the art and generally the dosage may be in a range of 0.01 mg/kg/day to approximately 2,000 mg/kg/day. A preferable dose is in a range of 1 mg/kg/day to 500 mg/kg/day. The composition may be administered once a day or several times a day. The dose does not limit the scope of the present disclosure in any respect.

The pharmaceutical composition may be administered to mammals such as rats, livestock, or humans through various routes. All modes of administration may be expected. For example, the administration may be by oral, rectal, or intravenous, intramuscular, subcutaneous, endocervical, or intracerebral injection. Since the compound of the present disclosure has little toxicity and side effects, h compound may be safely used for long-term use for preventive purposes.

The present disclosure relates to a health functional food composition for prevention or improvement of an allergic disease, wherein the health functional food compound may include an inotodiol compound or a chaga mushroom extract containing an inotodiol compound as an active ingredient and a food-acceptable food additive.

The health functional food compound may include the inotodiol compound or the chaga mushroom extract containing an inotodiol compound as an active ingredient in a range of 0.001 wt % to 100 wt %.

The health functional food may be in the form of a tablet, a capsule, a pill, or a liquid preparation. Food that may be added to the extract of the present disclosure, for example, various foods, beverages, gum, tea, and vitamin complexes.

Advantageous Effects of Disclosure

The present disclosure relates to a composition for prevention or treatment of an allergic disease, wherein the composition may include an inotodiol compound or a chaga mushroom extract containing the inotodiol compound as an active ingredient. It was found that when the inotodiol compound or the chaga mushroom extract containing an inotodiol compound as an active ingredient is administered to a food allergy induced-mouse model, symptoms induced by the allergy is alleviated and cured, and mast cell immunoreactivity is inhibited.

Accordingly, the inotodiol compound and the chaga mushroom extract including an inotodiol compound as an active ingredient is expected to be useful as a composition for prevention or treatment of an allergic disease.

BRIEF DESCRIPTION OF DRAWINGS

FIG. 1 shows allergy symptom improvement followed by food allergy induction and treatment with an inotodiol compound and a chaga mushroom fraction including an inotodiol compound.

FIG. 4 shows test results of CD4$^+$T cell immunoreactivity followed by food allergy induction and treatment with an inotodiol compound and a chaga mushroom fraction including an inotodiol compound.

BEST MODE

Figure 1A:
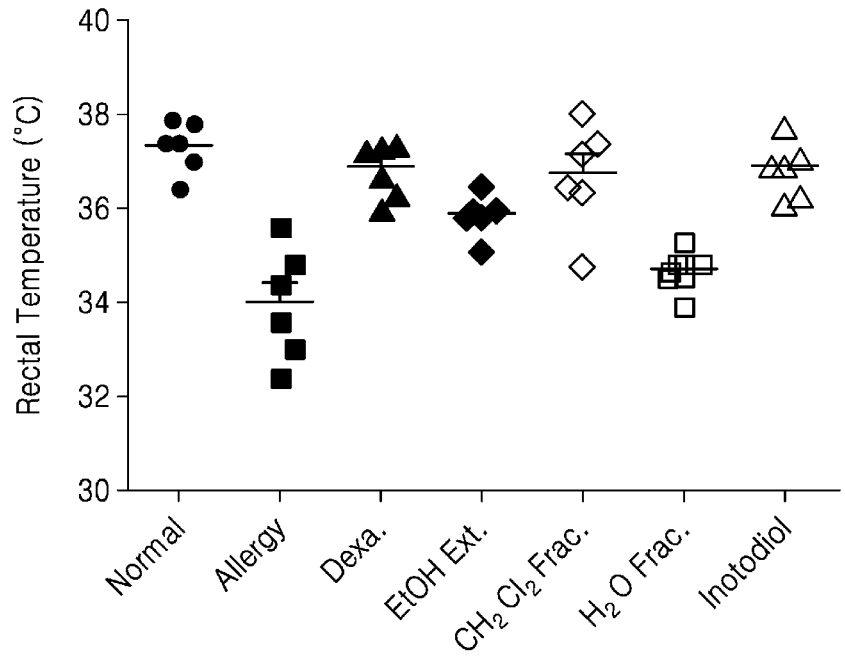
FIG. 1(A) shows change in rectal temperature.

Hereinafter, the present disclosure will be described in more detail with reference to preferable Examples. However, the present disclosure is not limited to the Example described herein but may be embodied in other forms. Rather, the Example are provided herein such that the description presented here is thorough and complete, and the concept of the present disclosure is fully conveyed to one of ordinary skill in the art.

Example 1. Isolation of Inotodiol Compound

Example 1-1. Preparation of Chaga Mushroom Extraction and Content Check of Inotodiol Compound The inotodiol compound of the present disclosure was isolated from a chaga mushroom (*Inonotus obliquus*) extract.

630 grams (g) of chaga mushroom was pulverized into fine particles, 3,000 mL of 70% [v/v] ethanol was added thereto, and extraction was performed under ultrasonic agitation at 40° C. and 90 hertz (Hz) three times to obtain 70% ethanol extract (3×3.0 liters (L)). Then, 58 g of dried brown 70% ethanol extract was obtained using a rotary evaporator 58 g of chaga mushroom 70% ethanol extract was dissolved in water, followed by addition of (dichloromethane, $CH_2Cl_2$) to obtain 6.0 g of a dichloromethane fraction. After isolating the dichloromethane fraction, ethyl acetate (EtOAc) was added to the remaining fraction to obtain 3.2 g of an ethyl acetate fraction and 48.5 g of a water fraction.

High performance liquid chromatography (HPLC) was performed to measure a content of the inotodiol compound included in the obtained chaga mushroom extract and the fractions. HPLC was performed under a condition of an acetonitrile concentration gradient (0-30 minutes; 60%→95% [v/v], 30-60 minutes; 95% [v/v] constantly) using LC-10AD (Shimadzu Co. Kyoto, Japan). Each of the chaga mushroom extract and the fraction were dissolved in methanol to a concentration of 2 mg/mL, followed by filtering with a 0.2 μm syringe filter. Then, 10 μL thereof was injected. A content of the inotodiol compound was measured using a column of HECTOR-M C18 (4.6×250 mm, 5 μm particle size, RStech, Korea), at a flow of 1 mL/minute, with UV detection (210 nm). As a result, it was found that about 1% of the inotodiol compound was present in the 70% ethanol extract (EtOH Ext.), 7.8% of the inotodiol compound was present in the dichloromethane fraction ($CH_2Cl_2$ Frac.), 0.9 of the inotodiol compound was present in the ethyl acetate fraction (EtOAc Frac.), and 0.05% of the inotodiol compound was present in the water fraction ($H_2O$ Frac.) having the lowest inotodiol compound content.

In the case of a chloroform fraction obtained by using chloroform instead of dichloromethane, the chloroform fraction was found to contain a similar amount of the inotodiol compound as the dichloromethane fraction.

Example 1-2. Isolation of Inotodiol Compound

The inotodiol compound was isolated from the dichloromethane fraction of chaga mushroom obtained in Example 1-1.

2.5 g of the dichloromethane fraction was subjected to fraction through silica gel column chromatography using 1 L of each of mixed solvents in which n-hexane was mixed with ethyl acetate at a ratio of 20:1, 9:1, 4:1, 2:1, and 1:2 [v/v] according to a concentration gradient dissolution condition, thereby obtaining 13 minor fractions (Frac. C1-C13). Frac. C6 was mixed with Frac. C7, and the mixture was subjected to silica gel column chromatography according to a solvent condition of a solution in which n-hexane is mixed with ethyl acetate at 20:1 [v/v], thereby isolating 210 mg of the inotodiol compound.

Example 2. Confirmation of Physicochemical Structure of Inotodiol Compound

Inotodiol;
White amorphous powder;
ESI-MS: [M+ Na]$^+$ 465.37 m/z ($C_{30}H_{50}O_2$: 442.27);
$^1$HNMR and $^{13}$C NMR (see Table 1 for the data);
According to the ESI-MS analysis result and $^{13}$C NMR data, the molecular formula was found to be $C_{30}H_{50}O_2$.
In $^{13}$C-NMR for inotodiol, 30 peaks of carbon were observed, and it was found that at peaks of $\delta_C$121.2, 134.0, 134.4, and 134.8, 2 double bonds were present, and at peaks of $\delta_C$ 73.2 and 78.7, 2 hydroxyl groups were present (see Table 2). In $^1$H-NMR spectrum (see Table 2), at 0.67, 0.76, 0.82, 0.88, 0.93, 1.60, and 1.69 (3H, s) a singlet methyl peak was observed, and at $\delta_H$ 0.88, a doublet methyl peak was observed. Also, an olefinic peak corresponding to H-24 was observed at θ$\delta_H$ 5.16 (1H, t, J=7.2 Hz), and a peak of oxymethine bound to oxygen was observed at $\delta_H$ 3.18 (1H, m, H-3) and at $\delta_H$ 3.65 (1H, H-22).

The above result was compared with data reported in a paper (Du. D., et al., 2011) to verify the structure of the inotodiol compound.

TABLE 1

|  | $\delta_C$ (100 MHz) | $\delta_H$ (400 MHz) |
|---|---|---|
| 1 | 35.4 | |
| 2 | 27.6 | |
| 3 | 78.7 | 3.18 (m, 1H) |
| 4 | 38.7 | |
| 5 | 50.2 | 0.94 (m, 1H) |
| 6 | 18.9 | |
| 7 | 26.3 | |
| 8 | 134.4 | |
| 9 | 134.0 | |
| 10 | 36.8 | |
| 11 | 20.8 | |
| 12 | 28.9 | |
| 13 | 44.5 | |
| 14 | 49.2 | |
| 15 | 30.7 | |
| 16 | 30.7 | |
| 17 | 47.0 | 1.55 (m, 1H) |
| 18 | 15.5 | 0.67 (s, 3H) |
| 19 | 18.0 | 0.93 (s, 3H) |
| 20 | 41.5 | 1.97 (m, 1H) |
| 21 | 12.4 | 0.88 (d, J = 6.5 Hz, 1H) |
| 22 | 73.2 | 3.65 (m, 1H) |
| 23 | 27.0 | |
| 24 | 121.2 | 5.16 (t, J = 7.2 Hz, 1H) |
| 25 | 134.8 | |
| 26 | 25.7 | 1.60 (s, 3H) |
| 27 | 17.9 | 1.69 (s, 3H) |
| 28 | 27.7 | 0.90 (s, 3H) |
| 29 | 15.2 | 0.76 (s, 3H) |
| 30 | 24.1 | 0.82 (s, 3H) |

Experimental Example 1. Preparation of Allergy Mouse Model and Administration of Extract To prepare allergy mouse models, 5-week-old male BALB/C mice were used. Food allergy models were prepared using ovalbumin of chicken as an allergy-inducing material (allergen).

For immunization of the mice, 20 μg of ovalbumin was mixed with 2 mg of alum, and the mixture was intraperitoneally injected to the mice two times every two weeks. Food allergy induction was induced by performing the second immunization injection and two weeks thereafter, 50 mg of ovalbumin was orally administered thereto five times every three days to cause an allergic response. In addition, to confirm allergy therapeutic effect, the chaga mushroom extract, the fraction, and the inotodiol compound obtained in Example 1 were orally administered to the mice every day during the administration period of ovalbumin. Here, as a positive control, a mice group was used to which dexamethasone was administered every day. 50 mg of ovalbumin alone or the chaga mushroom extract, the fraction, or the inotodiol compound was lastly administered thereto, followed by observation on symptoms caused by allergy one hour thereafter. For each experimental group, six mice were used, and each experimental group is shown in Table 2.

TABLE 2

| Group | Sample treatment |
|---|---|
| Normal | Not treated |
| Allergy induction | Ovalbumin (food allergy induction) |
| Positive control (Dexa.) | 20 mg/kg of ovalbumin and dexamethasone |
| EtOH Ext. | 320 mg/kg of ovalbumin and chaga mushroom 70% ethanol |
| $CH_2Cl_2$ Frac. | 320 mg/kg of ovalbumin and the dichloromethane fraction of |
| $H_2O$ Frac. | 320 mg/kg of ovalbumin and the water fraction of chaga |
| Inotodiol | 20 mg/kg of ovalbumin and inotodiol compound |

Experimental Example 2. Confirmation of Improvement in Allergy Symptoms

Experimental Example 2-1. Confirmation of Change in Rectal Temperature

In order to see the change in rectal temperature followed by food allergy induction and drug treatment, mice corresponding to each group were subjected to measurement of rectal temperature. Rectal temperature was measured by inserting the tip of the sensor of a rectal thermometer into rectum. The results thereof are shown in FIG. 1(A).

As shown in FIG. 1(A), it was found that an allergy-induced group (Allergy) had a lower rectal temperature than a normal group (Normal). On the other hand, it was found that the group treated with dexamethasone (Dexa.) or the group treated with the inotodiol compound isolated from chaga mushroom (Inotodiol), the group treated with the chaga mushroom ethanol extract including an inotodiol compound (EtOH Ext.), and the group treated with the dichloromethane fraction ($CH_2Cl_2$ Frac.) of the present disclosure had a higher rectal temperature than the food allergy-induced group (Allergy). In particular, the group treated with the inotodiol compound and the group treated with the dichloromethane fraction were found to have a similar level of rectal temperature with the normal group. On the other hand, the group treated with the water fraction of chaga mushroom ($H_2O$ Frac.) was found to have a similar level of rectal temperature with the food allergy-induced group.

Accordingly, it was found that the inotodiol compound and the dichloromethane fraction of chaga mushroom including an inotodiol compound of the present disclosure improved a low rectal temperature, i.e., one of the symptoms caused by allergy induction.

Experimental Example 2-2. Anaphylaxis Observation

Figure 1B:
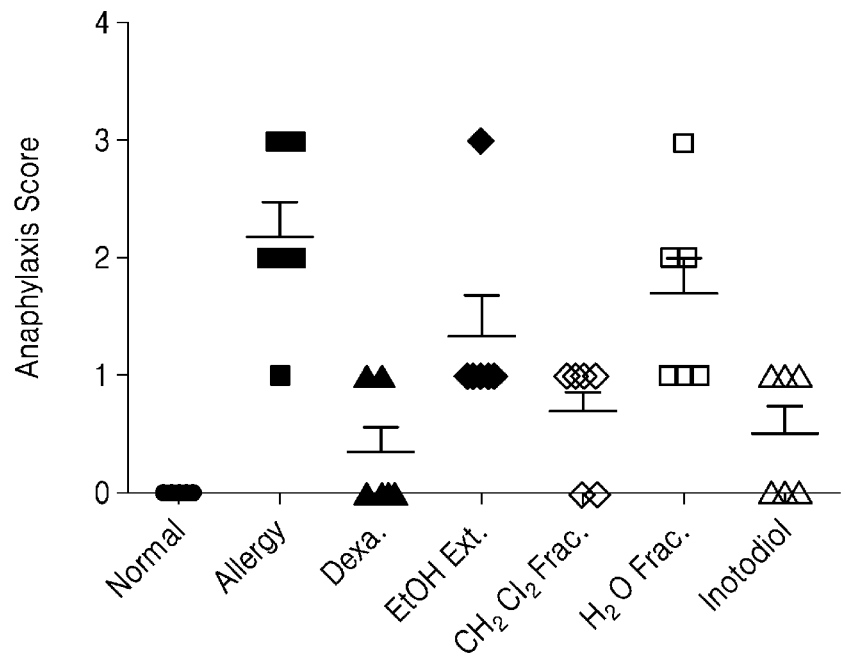
FIG. 1(B) shows a level of relief or treatment of anaphylaxis symptoms.

To see improvement or therapeutic effect of the inotodiol compound isolated from chaga mushroom and the dichloromethane fraction of chaga mushroom including the inotodiol compound of the present disclosure with regard to an anaphylaxis symptom caused by food allergy, responses of mice of each experimental group were observed, and the anaphylaxis symptoms were scored according to Table 3. The results thereof are shown in FIG. 1(B).

TABLE 3

| ANAPHYLAXIS SYMPTOMS | SCORE |
|---|---|
| NORMAL | 0 |
| SLOW RESPONSE | 1 |

TABLE 3-continued

| ANAPHYLAXIS SYMPTOMS | SCORE |
|---|---|
| NO RESPONSE | 2 |
| SHIVERING | 3 |
| DEATH | 4 |

As shown in FIG. 1(B), the food allergy-induced group (Allergy) had a higher anaphylaxis score than the normal group (Normal). On the other hand, the group treated with dexamethasone (Dexa.), the group treated with the chaga mushroom ethanol extract (EtOH Ext.), the group treated with the dichloromethane fraction ($CH_2Cl_2$ Frac.), and the group treated with the inotodiol compound (Inotodiol) had a lower anaphylaxis score than the food allergy-induced group. In particular, the group treated with the dichloromethane fraction of chaga mushroom and the group treated with the inotodiol compound were found to have lower anaphylaxis scores. On the other hand, the group treated with the water fraction of chaga mushroom ($H_2O$ Frac.) was found to have a similar level of an anaphylaxis score with the food allergy-induced group.

Accordingly, it was found that the inotodiol compound and the dichloromethane fraction of chaga mushroom including an inotodiol compound of the present disclosure improved anaphylaxis symptoms caused by allergy induction.

Experimental Example 2-3. Stool Observation in Large Intestine

Figure 1C:
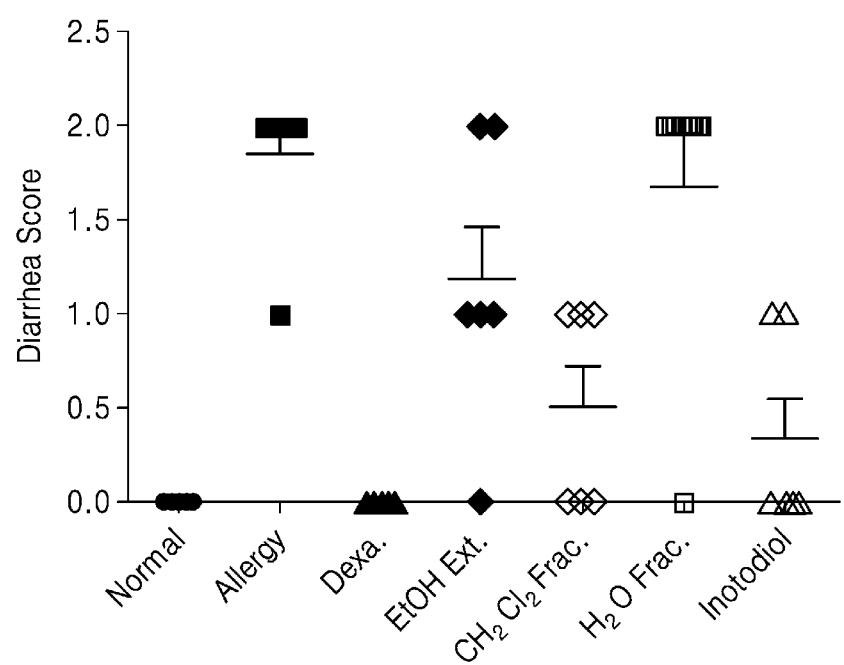
FIG. 1(C) shows diarrhea score.

The change in a stool shape was observed due to food allergy upon treatment with the inotodiol compound isolated from chaga mushroom and the dichloromethane fraction of chaga mushroom including the inotodiol compound of the present disclosure. The stool shapes in the large intestines of mice of each experimental group were observed with a naked eye, and the symptoms were scored according to Table 4, and the results thereof are shown in FIG. 1(C).

TABLE 4

| Diarrhea symptom | Score |
|---|---|
| Normal | 0 |
| Normal/watery stool | 1 |
| Frequent and uncontrolled watery stool | 2 |
| Severe diarrhea | 3 |
| Death | 4 |

As shown in FIG. 1(A), it was found that a food allergy-induced group (Allergy) had a higher diarrhea symptom score than a normal group (Normal). Scores of diarrhea symptoms of the group treated with dexamethasone (Dexa.) or the group treated with the inotodiol compound isolated from chaga mushroom (Inotodiol) and the group treated with dichloromethane fraction of chaga mushroom including an inotodiol compound ($CH_2Cl_2$ Frac.) were lower than that of the food allergy-induced group. On the other hand, the group treated with the chaga mushroom ethanol extract (EtOH Ext.) and the group treated with the water fraction ($H_2O$ FraC.) had smaller diarrhea symptom relief effects than the chaga mushroom dichloromethane fraction. In the case of the water fraction had a similar level of the allergy-induced group.

Accordingly, it was found that the inotodiol compound isolated from chaga mushroom and the dichloromethane fraction of chaga mushroom including an inotodiol compound of the present disclosure improved diarrhea symptoms caused by allergy induction.

Also, although it is not shown in FIG. 1, a group treated with the chloroform fraction of chaga mushroom showed a similar rectal temperature, anaphylaxis score, and stool symptom score as the dichloromethane fraction of the present disclosure. On the other hand, when a group is treated with 20 mg/kg of cholesterol, which has a similar structure as the inotodiol compound, it was found that unlike the inotodiol compound, the group showed a similar level of rectal temperature, anaphylaxis score, and stool symptom score as the allergy-induced group.

Therefore, through the rectal temperature, the anaphylaxis symptom, and the stool observation, the inotodiol compound isolated from chaga mushroom was found to be one of the main active ingredients that relieve allergy symptoms. In addition, the dichloromethane fraction and the chloroform fraction of chaga mushroom including the inotodiol compound as an active ingredient were found to have excellent allergy symptom relief effects.

Experimental Example 3. Observation on Changes in Cells in Small Intestine Due to Food Allergy Experimental Example 3-1. Observation on Eosinophil in Small Intestine Eosinophil is known to play an important role in food allergy. That is, eosinophil induces allergic inflammation in in small intestines. By observing eosinophil changes in small intestines, allergy prevention and therapeutic effects of the inotodiol compound and the dichloromethane fraction of chaga mushroom including the inotodiol compound of the present disclosure were confirmed.

The mice of each experimental group in Experimental Example 1 were anesthetized and cut the abdomen. Then, the small intestine was removed, fixed with formalin, treated with paraffin, permeated with paraffin, and microsectioned using microtome, thereby obtaining tissue sections. The obtained small intestine sections were stained with hematoxylin and eosin (H&E) to observe eosinophil cells. The results thereof are shown in FIG. 2(A).

Figure 2A:
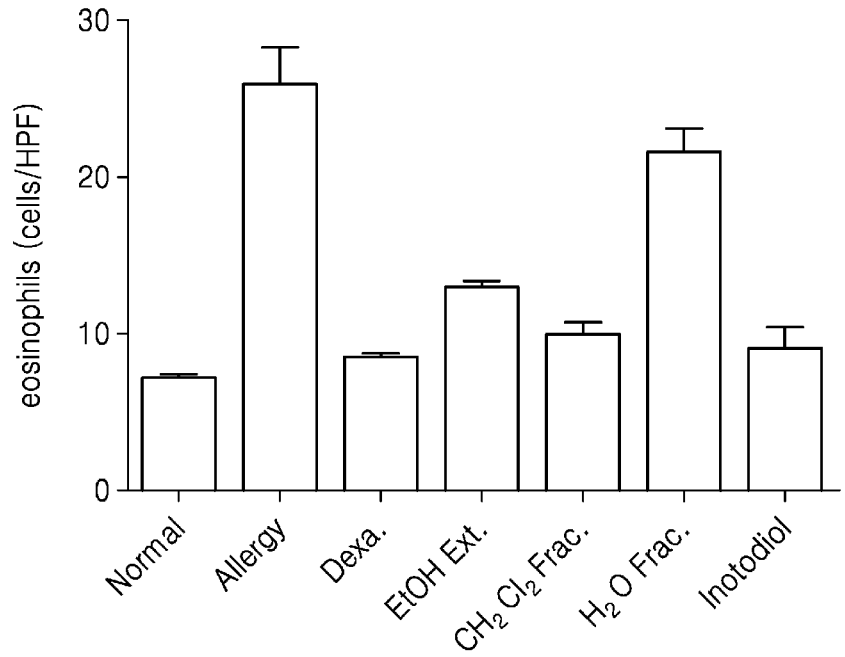
FIG. 2 shows change in (A) the number of eosinophils infiltrated in small intestine; and (B) the number of mast cells in the small intestine followed by food allergy induction and treatment with an inotodiol compound and a chaga mushroom fraction including an inotodiol compound.

According to the results of measurement of the number of stained eosinophil cells by tissue staining as shown in FIG. 2(A), the food allergy-induced group (Allergy) showed increased infiltration of eosinophils in the small intestine, as compared with the normal group, and the group treated with dexamethasone (Dexa.), the group treated with the inotodiol compound isolated from chaga mushroom (inotodiol), and the dichloromethane fraction including an inotodiol compound isolated from chaga mushroom ($CH_2Cl_2Fr_ac.$) showed decreased infiltration of eosinophils. However, the water fraction of chaga mushroom ($H_2O$ Frac.) had little decreasing effects.

Accordingly, it was found that the inotodiol compound isolated from chaga mushroom and the dichloromethane fraction of chaga mushroom including an inotodiol compound of the present disclosure prevent or treat allergy by alleviating inflammation caused by the allergy.

Experimental Example 3-2. Observation on Mast Cells in Small Intestine

By observing mast cells which are known as inducing an allergic response, allergy prevention and therapeutic effects of the inotodiol compound and dichloromethane fraction of chaga mushroom including the inotodiol compound fraction of the present disclosure were confirmed.

To observe mast cells, the tissue sections of small intestines obtained in Experimental Example 3-1 were stained with toluidine. Then, the mast cells were observed with a microscope, and the number of mast cells were measured, which are shown in FIG. 2(B).

Figure 2B:
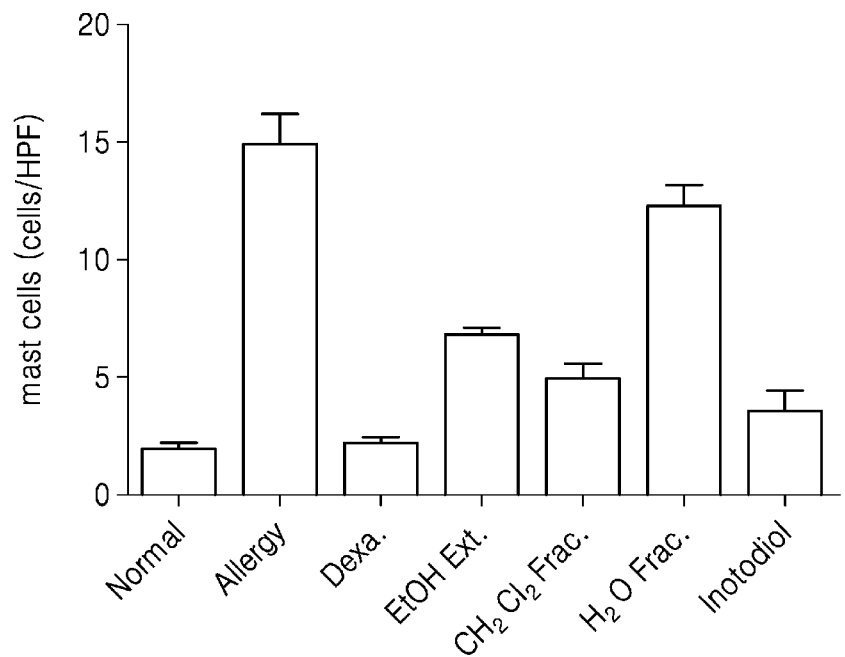

According to the results of measurement of the number of stained mast cells by toluidine staining as shown in FIG. 2(B), the food allergy-induced group (Allergy) showed increased number of mast cells in the small intestine, as compared with the normal group, and the group treated with dexamethasone (Dexa.), the group treated with the inotodiol compound isolated from chaga mushroom (Inotodiol), and the dichloromethane fraction including an inotodiol compound isolated from chaga mushroom ($CH_2Cl_2Fr_ac.$) showed decreased number of mast cells. However, the water fraction ($H_2O$ Frac.) had little decreasing effects.

Also, although it is not shown in FIG. 2, a group treated with the chloroform fraction showed a similar level of decrease in the number of eosinophils and mast cells as the dichloromethane fraction of chaga mushroom of the present disclosure. On the other hand, when a group is treated with 20 mg/kg of cholesterol, which has a similar structure as the inotodiol compound, it was found that unlike the inotodiol compound, the group showed little decrease in the number of eosinophils and mast cells.

Accordingly; it was found that the inotodiol compound isolated from chaga mushroom and the dichloromethane fraction of chaga mushroom including an inotodiol compound of the present disclosure prevent or treat allergy.

Experimental Example 4. Confirmation of Expression of IgE and MCPT-1 Due to Allergy An allergic response is due to expression of IgE responsive to allergen and by combination of allergen and IgE, mast cells secrete granular materials associated with allergic inflammation such as histamine, serine protease, or proteoglycan. Therefore, to confirm allergy prevention and therapeutic effect of the inotodiol compound and the dichloromethane fraction of chaga mushroom including the inotodiol compound of the present disclosure, a concentration of each of IgE and a mast cell protease-1 (MCPT-I), i.e., a mast cell-specific serine protease, in serum of a mouse was measured.

The serum was obtained from the blood of a mouse one day after administration of 50 mg of ovalbumin alone or the chaga mushroom extract, the fraction, or the inotodiol compound in Experimental Example 1. The obtained serum was diluted 100 times and used.

The IgE concentration in the serum was measured using an enzyme-linked immunosorbent assay (ELISA) kit. 100 µL of a carbonate coating buffer (pH 9.5) containing 2 µg/mL of ovalbumin was added to each well of a 96-well plate, and then subjected to reaction at a temperature of 4° C. overnight for coating. The plate was washed three times with a washing buffer (0.05% tween 20 in PBS), a phosphate buffered saline (PBS) containing 1% bovine serum albumin (BSA) was added to 200 µL per well, followed by treatment at room temperature for 1 hour and blocking. Thereafter, three times of washing with a washing buffer were carried out. After washing, 100 µL of serum was added to each well, reacted at room temperature for 2 hours, and washed with washing buffer. 100 µL of 1 µg/mL of biotin-conjugated anti-mouse IgE was added to each well and reacted for one hour, followed by washing with washing buffer and treatment with streptavidin-HRP to which a horseradish peroxidase (HRP) is conjugated for 30 minutes. The plate was washed five times with washing buffer, and 100 µL of tetramethylenbenzidine was treated to induce color development. After color development, 2N sulfuric acid ($H_2SO_4$) was added to each well to stop the color reaction. The absorbance at 450 nm was measured and the concentration of IgE in the serum was analyzed. The results thereof are shown in FIG. 3(A).

A concentration of a mast cell protease-1 (MCPT-1), i.e., a serine protease was measured using a mMCP-1 ELISA kit (eBioscience) according to the protocol provided by the manufacturer. The results thereof are shown in FIG. 3(B).

Figure 3A:
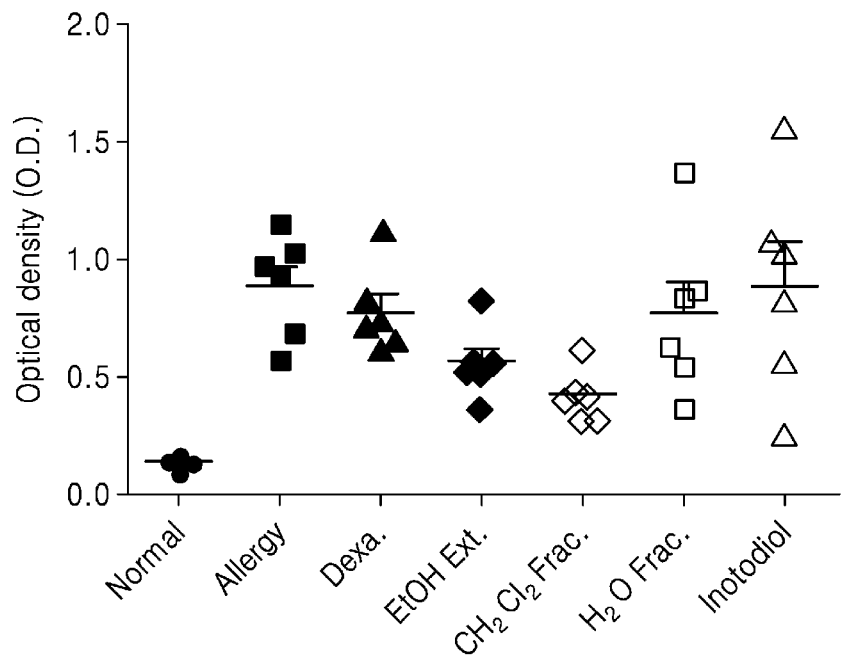
FIG. 3 shows change in concentration of allergy-related IgE (A); and MCPT-I (B) in a serum followed by food allergy induction and treatment with an inotodiol compound and a chaga mushroom fraction including an inotodiol compound.
Figure 3B:
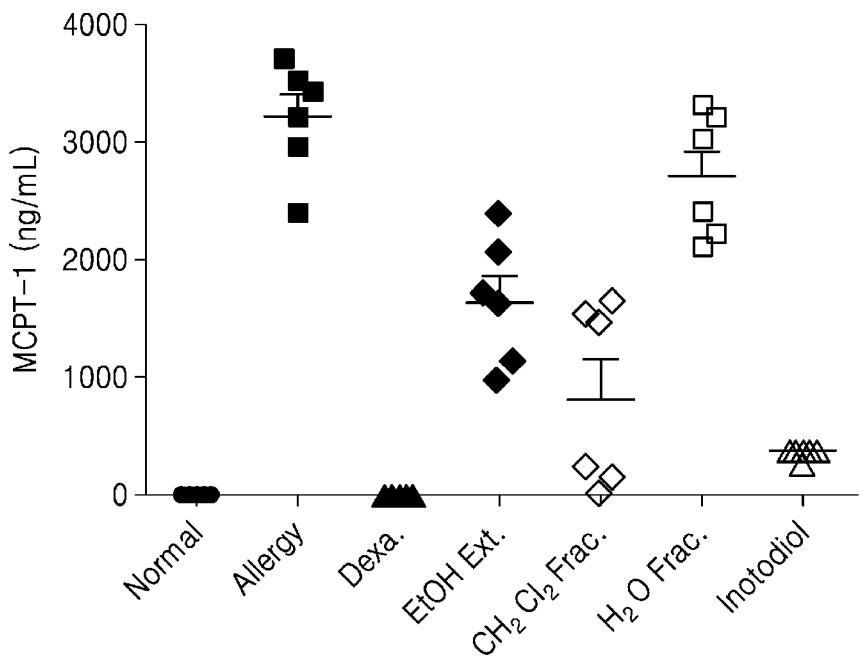

As shown in FIG. 3, the food allergy-induced group (Allergy) had increased concentrations of egg white protein-specific IgE (FIG. 3(A)) and MCPT-1 (FIG. 3(B)) in serum, as compared with the normal group (Normal). The group treated with the ethanol extract of chaga mushroom (EtOH Ext) and the group treated with the dichloromethane traction ($CH_2Cl_2$ Frac.) had significantly decreased concentrations of IgE and MCPT-1. The group treated with the water fraction of chaga mushroom ($H_2O$ Frac.) did not have substantial change in concentrations of IgE and MCPT-1. The group treated with dexamethasone (Dexa.) and the group treated with the inotodiol compound (inotodiol) had no substantial change in the concentration of IgE, however, the concentration of MCPT-1 of these groups decreased significantly.

Also, although it is not shown in FIG. 3, a group treated with the chloroform fraction showed a similar level of decrease in the concentration of IgE and MCPT-1 in serum as the dichloromethane fraction of chaga mushroom of the present disclosure.

This result shows that effects of activity regulation/inhibition of the mast cells are more directly related to prevention or treatment of allergy symptoms than the reducing effects of allergen specific IgE expression.

Experimental Example 5. Confirmation of Mast Cell-Specific Inhibition Effects

Experimental Example 5-1. Confirmation of $CD4^+$ T Cell Activity Regulation Effects It is known that cytokines produced by T helper 2 (Th2) $CD4^+$ T cells promote production of IgE and promote differentiation of mast cells and eosinophils, thereby deepening allergic symptoms. It has also been reported that plant extracts, which have been reported to have anti-allergic effects, have effects of inhibiting the activation of $CD4^+$ T cells and cytokine production of Th2 $CD4^+$ T cells.

In order to examine the effect of an inotodiol compound or a chaga mushroom extract containing an inotodiol compound on $CD4^+$ T cell activity regulation, analysis of expression level of cytokine produced by Th2 $CD4^+$ T cell and adoptive transfer experiments using $CD4^+$ TCR transgenic T cells that express DO11.00 TCR, i.e., the ovalbumin-derived peptide specific T cell receptor (TCR), were performed.

For the expression of cytokine, a sample was treated in the same manner as in Experimental Example 1, and the cells were isolated from the mesenteric lymph node (mLN) of mice of each group after one day. At this time, a group treated with 10 mg/kg of dexamethasone, a group treated with 20 mg/kg of imatinib (Gleevec), which is used as a mast cell hyperthermia therapeutic agent, and a group treated with 20 mg/kg of cholesterol that is similar in structure to the inotodiol compound were added. The isolated cells were dispensed into wells of a 96-well plate at a rate of 1×10⁶ cells/well. RPMI complete medium (containing 10% fetal bovine serum (FBS), penicillin, streptomycin, and glutamine) containing ovalbumin or RPMI complete medium containing 100 μg/mL of ovalbumin was inoculated and culture for three days under a condition of 37° C. and 5% $CO_2$. After three days, the cell culture solution was collected, followed by analysis using an ELISA kit according to the protocol provided by the manufacturer to analyze amount of IL-5, IL-13, and IFN-γ corresponding to each cytokine secreted as a cell culture solution. The results thereof are shown in FIG. 4 (A).

Experiments to measure a degree of ovalbumin-derived peptide specific T cell immune response from an animal experiment were performed as follows. Cells were isolated from the lymph nodes of transgenic mice expressing DO11.10TCR. The isolated cells were fluorescence-stained with carboxyfluorescein succinimidyl ester (CFSE), and 2×10⁶ cells were injected intravenously into BALB/C mice. Cells were injected intraperitoneally with ovalbumin (50 μg) and alum to induce division of CD4⁺ T cells expressing DOII.00 TCR. Oral administration of 20 mg/kg of the inotodiol compound, 320 mg/kg of the chaga mushroom ethanol extract, 10 mg/kg of dexamethasone, 10 mg/kg of imatinib, or 20 mg/kg of the cholesterol was performed once a day for four days starting from one day after ovalbumin injection. After five days of ovalbumin injection, the cells were isolated from BALB/C lymph nodes, stained with anti-CD4 antibody and anti-DO11.10 antibody, and measured CFSF fluorescence intensity of the CD4⁺ T cell expressing DOII.00 TCR using flow cytometry to determine the cell division degree. Then, the number of cells was measured. The results thereof are shown in FIG. 4(B), respectively. Here, the CFSF fluorescence intensity decreased as the cell division increases.

Figure 4A:
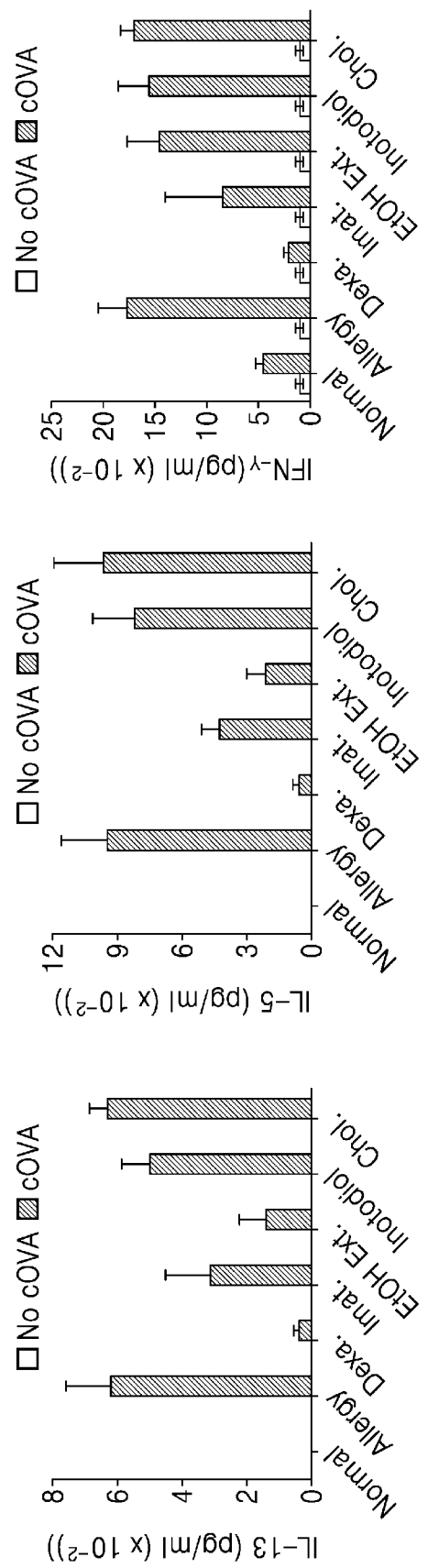
FIG. 4(A) shows expression changes in IL-13, IL-5, and IFN-$\gamma$, which are cytokine produced by Th2 CD4$^+$T cells.
Figure 4B:
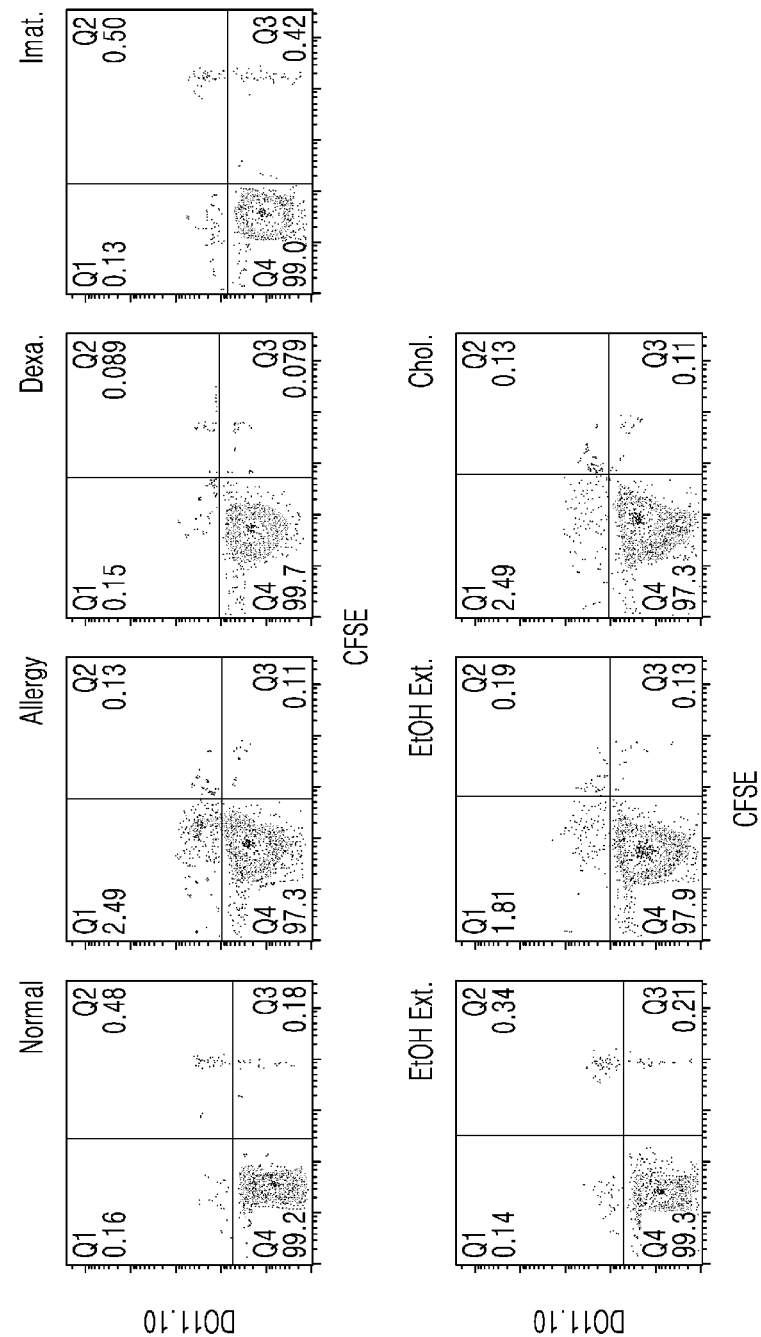
FIG. 4(B) shows a level of activation by ovalbumin of CD4$^+$T cells expressing DO11.00 TCR, i.e., an ovalbumin-derived peptide-specific T cell receptor and a level of the following cell division.

As shown in FIG. 4(A), no substantial expression of IL-5, IL-13, and IFN-γ in all groups was observed in the case of cells cultured in RPMI complete medium without ovalbumin (No OVA). However, in the case of cells cultured in RPMI complete medium including ovalbumin (OVA), the amount of each of IL-5, IL-13, and IFN-γ was increased in the allergy-induced group (Allergy). However, the amount of cytokine of the group treated with the chaga mushroom ethanol extract (EtOH Ext.) was similar to that of the normal group (Normal). However, the amount of cytokines of the group treated with the inotodiol compound (Inotodiol) was not substantially different from the expression amount of IL-5, IL-13, and IFN-γ.

In addition, as in the analysis of CD4⁺ T cell expressing DO11.00 TCR, i.e., an ovalbumin-derived peptide specific TCR shown in FIG. 4(B), the group treated with ovalbumin (Allergy) had a significantly decreased CFSE fluorescence intensity of CD4⁺T cell expressing DOII.00 TOR of and a significantly increased number of CD4⁺T cells, as compared with the ovalbumin-unimmune group (Normal). However, the group treated with chaga mushroom ethanol extract (EtOH Ext.) and the group treated with imatinib (Imat.) had no difference in the CFSE fluorescence intensity and the number of cells, as compared with the unimmune group. The group treated with the inotodiol compound (Inotodiol) had a similar level of decrease in CFSE fluorescence intensity of CD4⁺T cell expressing DOII.00 TCR, as compared with the group treated with ovalbumin, and significantly increased number of CD4⁺T cells.

Also, although it is not shown in FIG. 4, a group treated with the dichloromethane fraction of chaga mushroom and a group treated with the chloroform fraction of chaga mushroom according to the present disclosure were found to inhibit cytokine expression due to Th2 CD4⁺T cells so does the chaga mushroom extract.

Accordingly, from the foregoing results, it was found that the dichloromethane fraction of chaga mushroom and the chloroform fraction of chaga mushroom according to the present disclosure have significant Th2 CD4⁺T cells (induced by allergen) activity regulating ability, while the inotodiol compound does not.

Experimental Example 5-2. Confirmation of Mast Cell Immunoreactivity Regulation Effects In Experimental Example 4, it was found that MCPT-1 expression reduction of an inotodiol compound or a chaga mushroom extract containing an inotodiol compound is related to immunoreactivity inhibition of mast cells due to an inotodiol compound.

In order to confirm degranulation inhibition effects of mast cells of the inotodiol compound or the chaga mushroom extract containing the inotodiol compound of the present disclosure, a passive systemic anaphylaxis experiment was performed.

the inotodiol compound (20 mg/kg), the chaga mushroom ethanol extract (320 mg/kg), cholesterol (20 mg/kg) similar in structure to the inotodiol compound, dexamethasone (10 mg/kg) as a positive control, and imatinib (20 mg/kg) were oral-administered to 5-week old male BALB/C mice of Experimental Example 1 once a day for 3 days. On the third day after oral administration, 3 μg of anti-dinitrophenol (DNP)-IgE was intravenously injected, and after 24 hours, mast cell degranulation was induced by intravenous injection of 80 μg of DNP-conjugated bovine serum albumin (BSA). The rectal temperature of mice induced mast cell degranulation was measured, and the amount of MCPT-1 in the blood was analyzed. The results thereof are shown in FIG. 5.

Figure 5A:
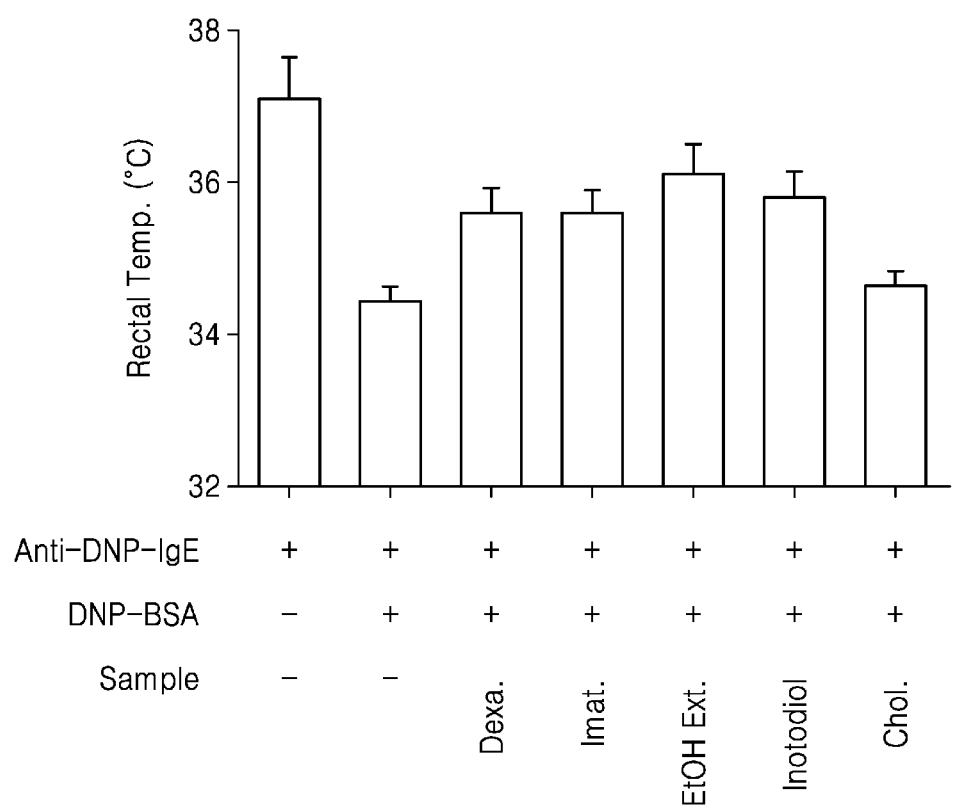
FIG. 5 shows test results of immunoreactivity of mast cells followed by food allergy induction and treatment with an inotodiol compound and a chaga mushroom fraction including an inotodiol compound, and shows the change in rectal temperature in mice in which degranulation of mast cells is induced (A) and the change in MCPT-1 in blood, by a passive systemic anaphylaxis method.

As shown in FIG. 5, upon measurement of the rectal temperature of mice (FIG. 5(A)), when the mast cell degranulation was induced (DNP-BSA treated) the temperature of the rectum was lowered, whereas the inotodiol compound (Inotodiol) and the chaga mushroom ethanol extract (EtOH Ext.) did not decrease the rectal temperature.

Figure 5B:
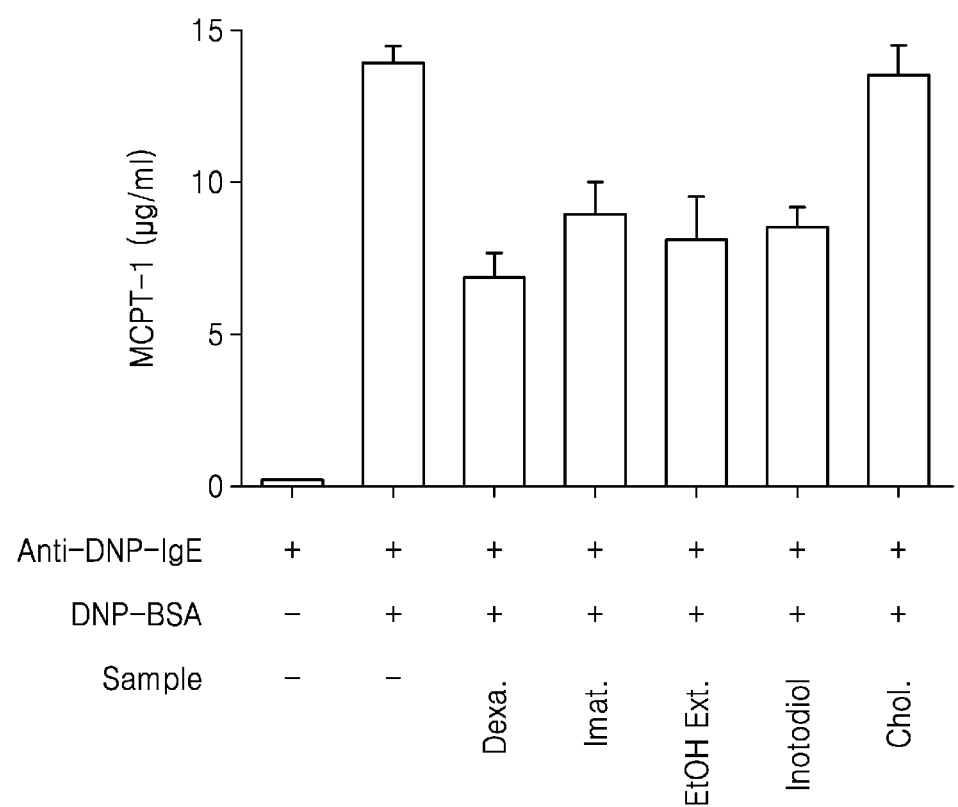

In addition, the amount of MCPT-1 secreted during mast cell degranulation was analyzed (FIG. 5(B)), and when the mast cell degranulation was induced (DNP-BSA treated), the concentration of MCPT-1 in the blood of the mouse increased. When treated with dexamethasone (Dexa.), imatinib (Imat.), the inotodiol compound (Inotodiol), and the chaga mushroom ethanol extract (EtOH Ext.), a level of increase in concentration of MCPT-1 was significantly decreased. When cholesterol that is similar in structure to the inotodiol compound (Chol.) is treated, unlike the inotodiol compound, MCPT-1 did not decrease.

Although it is not shown in FIG. 5, the dichloromethane fraction of chaga mushroom and the chloroform fraction of chaga mushroom according to the present disclosure inotodiol compound also reduced the amount of MCPT-1 to a similar degree.

Accordingly, it was found that the dichloromethane fraction of chaga mushroom and the chloroform fraction of chaga mushroom according to the present disclosure inhibited mast cell degranulation.

Therefore, from the foregoing results, it was found that the chaga mushroom dichloromethane fraction and chloroform fraction according to the present disclosure regulate CD4⁺T cell activity and inhibit mast cell degranulation, thus having multiple immune inhibition. On the other hand, unlike dexamethasone or the dichloromethane fraction and the chloroform fraction having multiple immune inhibition, the inotodiol compound according to the present disclosure selectively inhibit mast cell degranulation, thus providing a relatively selective and safe treatment of an allergic disease.

Preparation Example 1. Pharmaceutical Preparation

Preparation Example 1-1. Preparation of Tablet 200 g of the dichloromethane fraction of chaga mushroom according to the present disclosure was mixed with 175.9 g of lactose, 180 g of potato starch, and 32 g of colloidal silicic acid. A 10% gelatin solution was added to this mixture which was then pulverized and passed through a 14-mesh sieve. The result was dried, and 160 g of potato starch, 50 g of talc, and 5 g of magnesium stearate were added thereto to prepare a mixture which was then made into tablets.

Preparation Example 1-2. Preparation of Injectable Solution 1 g of the inotodiol compound of the present disclosure, 0.6 g of sodium chloride, and 0.1 g of ascorbic add were dissolved in distilled water such that the solution was 100 mL. The solution was added to a bottle and heated for 30 minutes at 20° C. for sterilization.

Preparation Example 2. Food Preparation

Preparation Example 2-1. Preparation of Cooking Seasonings

The inotodiol compound of the present disclosure was added to a cooking seasoning at 1 wt % to prepare a cooking seasoning for health promotion.

Preparation Example 2-2. Preparation of Flour Food

The inotodiol compound of the present disclosure was added to wheat flour at 0.1 wt %, and bread, cake, cookies, crackers, and noodles were prepared by using this mixture to prepare food for health promotion.

Preparation Example 2-3. Preparation of Soups and Gravies

The inotodiol compound of the present disclosure was added to soups and gravies at 0.1 wt % to prepare soups and gravies for health promotion.

Preparation Example 2-4. Preparation of Dairy Products

The inotodiol compound of the present disclosure was added to milk at 0.1 wt %, and this milk was used to prepare various dairy products such as butter and ice cream.

Preparation Example 2-5. Preparation of Vegetable Juice 0.5 g of the inotodiol compound of the present disclosure was added to 1,000 mL of tomato juice or carrot juice to prepare vegetable juice for health promotion.

Preparation Example 2-6. Preparation of Fruit Juice 1 g of the inotodiol compound of the present disclosure was added to 1,000 mL of apple juice or grape juice to prepare fruit juice for health promotion.

The invention claimed is:

1. A method for preventing or treating an allergic disease, the method comprising administering to a subject in need thereof a therapeutically effective amount of a chaga mushroom (*Inonotus obliquus*) extract including an inotodiol compound represented by Formula 1 as an active ingredient.

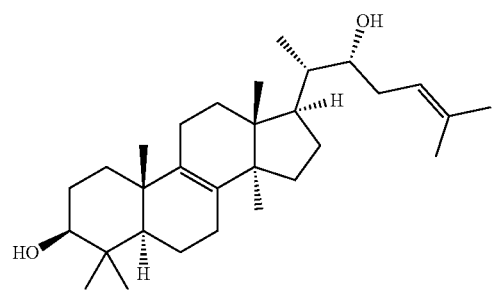

[Formula 1]

2. The method of claim 1, wherein the chaga mushroom extract is at least one selected from the group consisting of dichloromethane fractions or chloroform fractions obtained by adding dichloromethane or chloroform to an extract obtained by extracting chaga mushroom with 70 percent (%) ethanol as a solvent, respectively.

3. The method of claim 1, wherein the method suppresses degranulation of mast cells.

4. The method of claim 1, wherein the allergic disease is induced by at least one selected from the group consisting of pollen, medicines, vegetable fibers, bacteria, food, dyes, and chemicals.

5. The method of claim 4, wherein the allergic disease is induced by food.

6. The method of claim 1, wherein the allergic disease is at least one selected from the group consisting of urticaria, anaphylaxis, allergic rhinitis, bronchial asthma, and atopic dermatitis.

7. A method for preventing or treating an allergic disease, the method comprising administering to a subject in need thereof a therapeutically effective amount of an inotodiol compound represented by Formula 1 as an active ingredient.

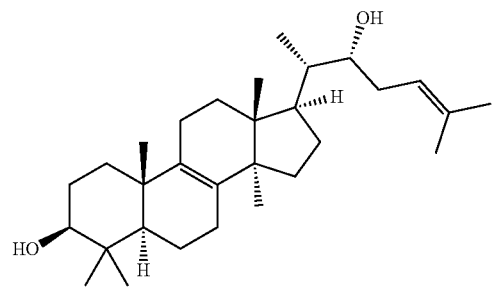

[Formula 1]

8. The method of claim 7, wherein the method suppresses degranulation of mast cells.

9. The method of claim 7, wherein the allergic disease is induced by at least one selected from the group consisting of pollen, medicines, vegetable fibers, bacteria, food, dyes, and chemicals.

10. The method of claim 9, wherein the allergic disease is induced by food.

11. The method of claim 7, wherein the allergic disease is at least one selected from the group consisting of urticaria, anaphylaxis, allergic rhinitis, bronchial asthma, and atopic dermatitis.

\* \* \* \* \*